United States Patent [19]

Cocuzza et al.

[11] 4,169,856

[45] Oct. 2, 1979

[54] PROCESS FOR THE PREPARATION AND THE RECOVERY OF ETHANOLAMINES

[75] Inventors: Gioacchino Cocuzza, Catania; Gianni Torreggiani, Busto Arsizio, both of Italy

[73] Assignee: Euteco S.p.A., Milan, Italy

[21] Appl. No.: 943,498

[22] Filed: Sep. 18, 1978

[51] Int. Cl.$^2$ .................. C07C 89/02; C07C 89/04
[52] U.S. Cl. .................. 260/585 B; 422/187
[58] Field of Search ............ 260/585 B, 584 R, 583 N

[56] References Cited

U.S. PATENT DOCUMENTS

| | | | |
|---|---|---|---|
| 2,051,486 | 8/1936 | Kautter | 260/584 R X |
| 2,182,807 | 12/1939 | Hasche | 260/585 B |
| 2,196,554 | 4/1940 | Guinot | 260/584 R |
| 2,373,199 | 4/1945 | Schwoegler et al. | 260/584 R |
| 2,823,236 | 2/1958 | Lowe et al. | 260/585 B X |
| 3,068,290 | 12/1962 | Lichtenberger et al. | 260/585 B X |
| 3,270,059 | 8/1966 | Winderl et al. | 260/585 B X |
| 3,723,530 | 3/1973 | Goetze et al. | 260/584 R |
| 4,112,231 | 9/1978 | Weibull et al. | 260/573 X |

FOREIGN PATENT DOCUMENTS

| | | | |
|---|---|---|---|
| 540033 | 4/1957 | Canada | 260/584 R |
| 763434 | 12/1956 | United Kingdom | 260/584 R |
| 763932 | 12/1956 | United Kingdom | 260/584 R |

*Primary Examiner*—Winston A. Douglas
*Assistant Examiner*—John Doll
*Attorney, Agent, or Firm*—Sughrue, Rothwell, Mion, Zinn and Macpeak

[57] ABSTRACT

A process for the preparation of ethanolamines includes passing ammonia in counter-flow with water and a recycled ammoniacal solution through an absorption column provided with internally cooled bubbling-trays to obtain an ammoniacal solution containing from 20 to 50% by weight of ammonia, reacting the ammoniacal solution with ethylene oxide firstly in an isothermal reactor and then in an adiabatic reactor to obtain substantially complete conversion of the ethylene oxide to ethanolamines, removing by means of a desorption column and recycling unreacted ammonia and part of the water from the reaction product, evaporating a greater part of the remaining water in an evaporator and dehydrating the ethanolamines at low pressure.

8 Claims, 5 Drawing Figures

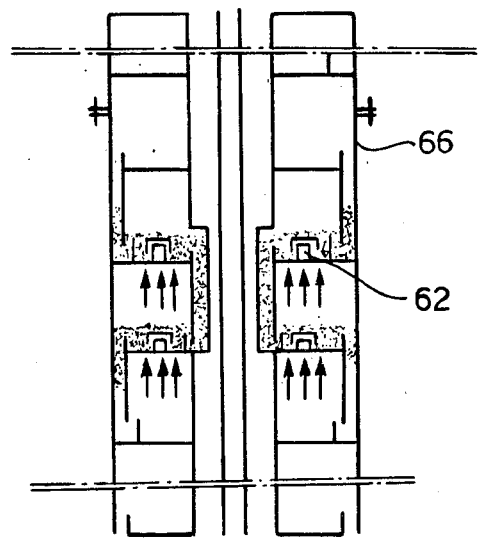
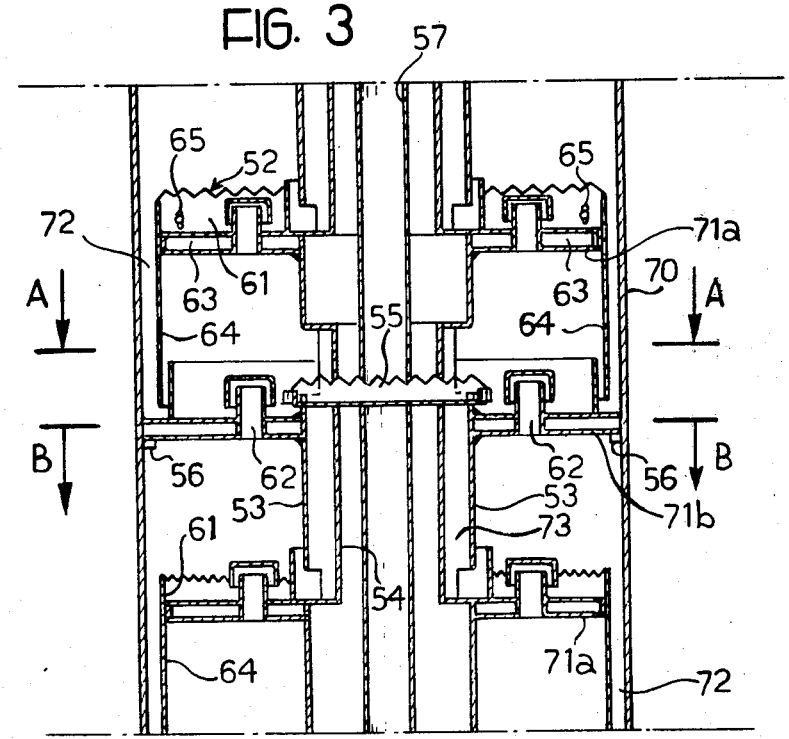

PROCESS FOR THE PREPARATION AND THE RECOVERY OF ETHANOLAMINES

BACKGROUND OF THE INVENTION

The present invention relates to an improved process for the preparation of ethanolamines by means of ammonolysis of ethylene oxide, and particularly to a process including the reaction of ethylene oxide with aqueous ammonia to give the mono-, di- and tri-ethanolamines.

Ethanolamines, either singly, or mixed together, are very useful products in the art. Thus, for example, tri-ethanolamine is an excellent corrosion inhibitor and mono- and di-ethanolamine, mixed together, are used in various industrial processes for the recovery of sulphuric acid and carbon dioxide from gaseous mixtures. The ethanolamines are also used as primary materials in various syntheses in the pharmaceutical industry and are reacted with fatty acids in the production of widely-used emulsifying substances.

According to the known art, ethanolamines may be prepared by ammonolysis of halohydrins or ethylene oxide, although the ethylene oxide is more widely used in commercial processes.

Thus, according to a known process, ethylene oxide and ammonia are brought into contact in a reaction chamber maintained at a temperature within the range of from 50° to 275° C. Normally relatively low temperatures, generally from 50° to 100° C., are preferred, the ethylene oxide being reacted with aqueous ammonia.

A mixture of reaction products is obtained including the mono-, di- and tri-ethanolamines, the ratio between these compounds depending on the ratio of the reagents used. For example, when excess ammonia is used with respect to the stoichiometric quantity, the reaction product is mainly monoethanolamine, while an excess of ethylene oxide favours the formation of tri-ethanolamine. In neither case is it possible, however, to obtain a single ethanolamine and, in the following description, the terms "ethanolamine" and "ethanolamines" will be understood to include the mono-, di- and tri-ethanolamines.

In known processes, the products from the reaction of ethylene oxide with ammonia are conveyed to desorption apparatus, where the excess ammonia and the greater part of the water are eliminated from the ethanolamine solution by heating at a pressure slightly greater than atmospheric.

A concentrated aqueous solution of the ethanolamines is discharged from the bottom of the desorption apparatus and conveyed to dehydrating apparatus where the residual water is removed, usually at a pressure lower than atmospheric. The ethanolamines are recovered from the bottom of the dehydrating apparatus and, if the individual components are required, these may be separated by fractional distillation.

The excess ammonia emitted at the head of the desorption apparatus is usually recovered, for example, by absorption in water in apparatus operated at a pressure about equal to that of the desorption apparatus. In fact, it is the absorption of ammonia in water to provide one of the starting materials for the reaction of the present invention which has caused some of the greatest technical problems in the prior art. This is due to the fact that the maximum concentration of ammonia absorbed in water depends not only on the pressure at which absorption is carried out but also on the absorption temperature, and in order to increase the concentration of ammonia, the solution must be cooled.

For this purpose, it is known to use an absorption column having plates provided with cooling coils. Given the small diameter of the columns needed for an ethanolamine plant of medium capacity, however, the provision of cooled plate columns of this type presents constructional difficulties and in any case such coils are not usually able to ensure homogeneous cooling of the aqueous solution. The use of filled columns of small diameter has, therefore, been proposed for the absorption of the ammonia, but the removal of heat from the solution in such apparatus, whether by external cooling jackets or by internal coils, is not readily controllable. This is because of the difficulties of heat transfer, with the small hold-up values in such columns, as well as the presence of the filling bodies themselves.

Other processes such as those in which the absorption liquid is removed from the column at an intermediate position, is cooled externally of the column and then reintroduced have also been tried and found unsatisfactory; in the particular case cited, the apparatus is complicated by the need to introduce devices for the removal of the solution from the column and for its subsequent reintroduction. Even the adoption of the system known as "pump around" for the aqueous ammoniacal solution leaving the column, has disadvantages in that it does not allow the total recovery of the ammonia, given that the gaseous phase leaving the column is in equilibrium with an aqueous solution already rich in ammonia.

According to a further known method the absorption of the ammonia is effected in an exchanger having a cooled, falling film in counter-flow with water. This solution has, among others, disadvantages typical of falling-film exchangers, such as, for example, the difficulty of achieving a homogeneous distribution of the liquid film in the exchanger tube and the necessity of operating with equi-current flows of gas and liquid, which is scarcely suitable for absorption operations.

Hence, bearing in mind that, in the processes under consideration, the absorption apparatus is connected to the desorption apparatus and is operated at a pressure slightly less than that of the latter, that is, close to atmospheric pressure, the use of absorption apparatus of any of the types described above results, inevitably, in low concentrations of the ammonia in the aqueous ammoniacal solution sent to the ammonolysis reactor. This, in turn, results in large quantities of the solution being employed since the ammonia is often required to be in excess with respect to the ethylene oxide, and hence large quantities of water vapour must later be removed in the dehydration stage, with commensurate increase in the energy used in the process.

In an alternative known method, the removal of large quantities of water in the dehydration stage is avoided by the use of concentrated aqueous solutions of ammonia, obtained by absorption at low temperatures, in the reaction with ethylene oxide. This method, however, requires the use of an expensive cooling cycle in the absorption stage.

The object of the present invention is, therefore, to provide a process for the preparation of ethanolamines by ammonolysis of ethylene oxide with aqueous ammonia and for the recovery of the said ethanolamines from the reaction products which is simple and convenient and which substantially reduces the disadvantages of the previous methods, especially those relating to the consumption of energy during the dehydration of the ethanolamines.

SUMMARY OF THE INVENTION

According to the present invention there is provided a process for the preparation of ethanolamines by ammonolysis of ethylene oxide with aqueous ammonia and for the recovery of said ethanolamines, including the steps of:

(a) preparing an aqueous ammoniacal solution containing from 20–50% by weight of ammonia by passing ammonia through an absorption column of the bubbling-tray type operating at a temperature of from 10° C. to 40° C. and at an absolute pressure of from 1.5 to 4 kg/cm$^2$, in counter-flow with water and a recycled aqueous ammoniacal solution, each of the bubbling-trays being individually cooled to maintain the absorption temperature within the range of from 10° to 40° C.;

(b) reacting said aqueous ammoniacal solution prepared in stage (a) with ethylene oxide in an isothermal reactor at a temperature of from 50° to 110° C., at an absolute pressure of from 10 to 30 kg/cm$^2$ and with an ammonia/ethylene oxide molar ratio of from 1/1 to 8/1, until at least 50% conversion of the ethylene oxide is achieved;

(c) feeding the reaction mixture from stage (b) into an adiabatic reactor and continuing the ammonolysis reaction until the conversion of said ethylene oxide to said ethanolamines is substantially complete, said ammonolysis reaction being carried out with a maximum temperature at the outlet from said adiabatic reactor of the order of 180° C.;

(d) removing the unreacted ammonia and a proportion of the water present in the reaction product of stage (c) by heating at an absolute pressure of from 0.5 to 1.0 kg/cm$^2$, condensing the aqueous ammoniacal vapors thus evolved, and recycling the aqueous ammoniacal solution thus obtained to stage (a);

(e) evaporating water from the residual aqueous solution of ethanolamines recovered in stage (d) in an evaporator at a pressure slightly greater than atmospheric and recycling the water vapour produced to provide heat for use in stage (d), and recovering a solution of ethanolamines having a water content not greater than 30% by weight; and (f) dehydrating said solution of ethanolamines recovered in stage (e) in a distillation column operated at a pressure lower than atmospheric, condensing the distillate from the head and using a part of the resulting condensate to wash the vapors at the head of said evaporator in stage (e) with consequent removal of the ethanolamine vapours contained therein, and recovering the dehydrated ethanolamines at the foot of said distillation column.

BRIEF DESCRIPTION OF THE DRAWINGS

The process of the present invention will now be more particularly described, by way of example, with reference to the attached drawings, in which:

FIG. 2 is a diagrammatic, vertical sectional view of apparatus for the absorption of ammonia forming part of the plant of FIG. 1;

FIG. 3 is a vertical sectional view, on a larger scale, of the apparatus of FIG. 2, taken on line C—C of FIG. 5;

DESCRIPTION OF THE PREFERRED EMBODIMENT

Figure 1:
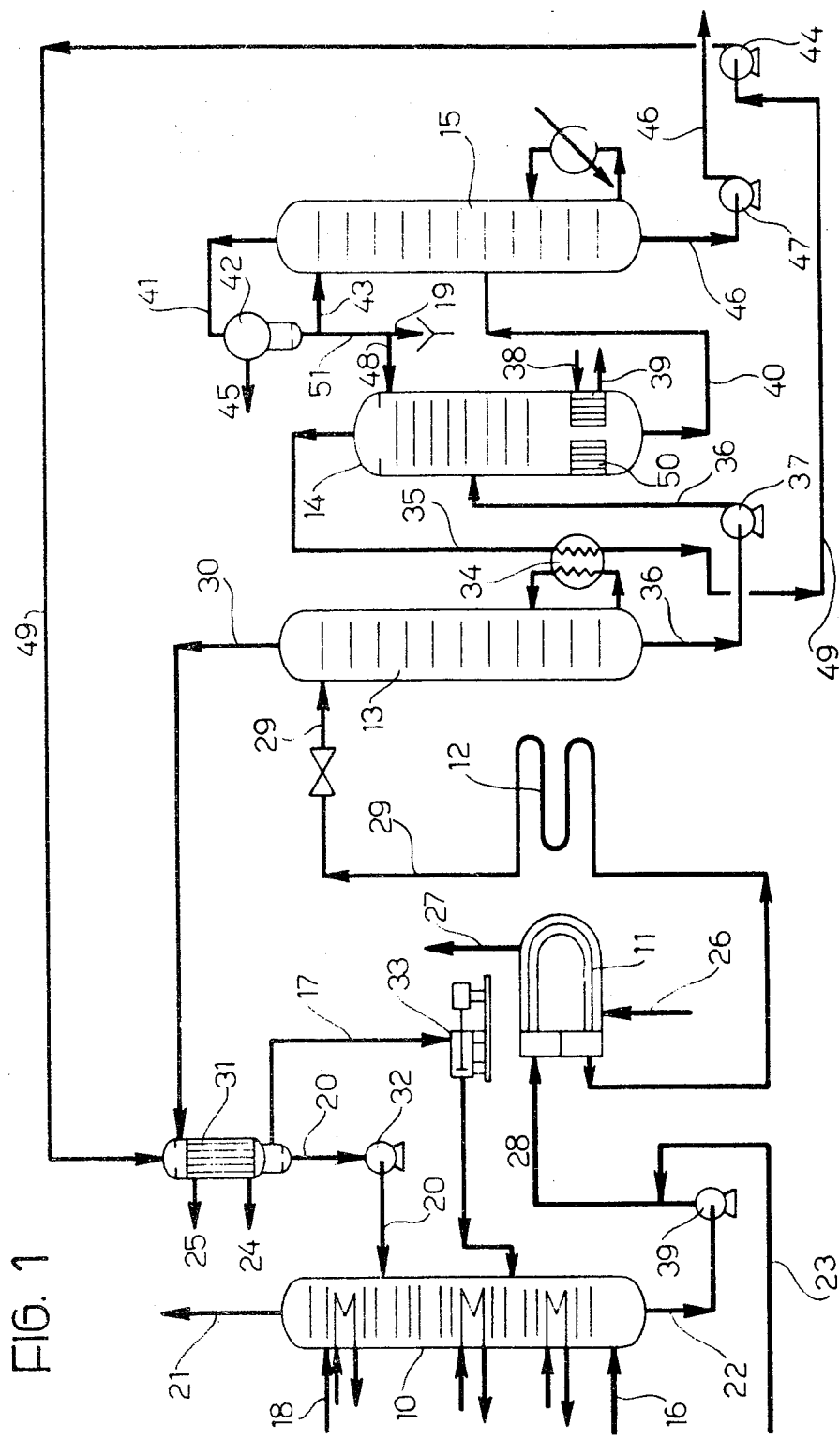
FIG. 1 is a schematic representation of a plant for carrying out the process of the present invention.
Figure 4:
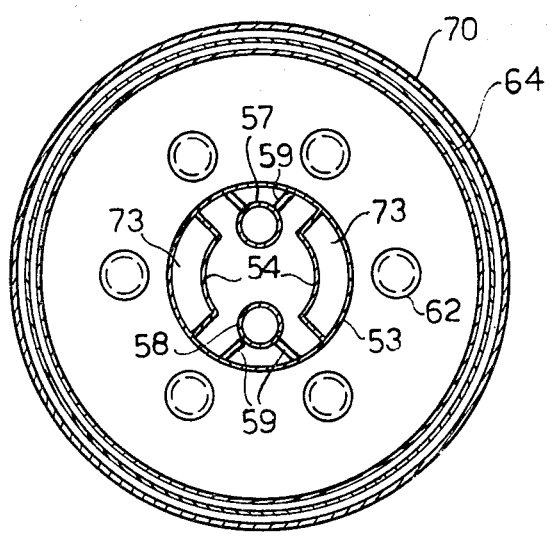
FIG. 4 is a horizontal sectional view taken on line A—A of FIG. 3.

Referring to FIG. 1 of the drawings, a plant for carrying out the process of the present invention is shown including a plate-type column 10 for the absorption of ammonia in water, an isothermal reactor 11 for the reaction of aqueous ammonia with ethylene oxide, an adiabatic reactor 12 for completing the reaction, a plate-type column 13 for removing excess ammonia from the reaction products, an evaporator 14 for removing water and a dehydrating column 15.

In use of the plant of FIG. 1, cold gaseous ammonia is fed to the foot of the water-cooled absorption column 10 through a line 16, while recycled ammonia is fed to the column 10 through a line 17. The ammonia flows upwardly through the column 10 in counter-flow with make-up water fed to the head of the column 10 through the line 18 and a recycled aqueous ammoniacal solution having an ammonia content of the order of 20% by weight fed to the column through a line 20. Cooling is preferably such that the operating temperature in the column 10 is of the order of 20° C. and an aqueous ammoniacal solution having an ammonia content typically of the order of 35% by weight is discharged at the foot through the line 22. Uncondensed gases are discharged at the head through a line 21.

The aqueous ammoniacal solution is mixed with ethylene oxide fed through the line 23, such that the ammonia/ethylene oxide molar ratio is of the order of 3/1 and the mixture is pumped through line 28 to the reactor 11 by means of the pump 39.

The isothermal reactor 11 consists of a bundle of U-tubes, maintained at a temperature typically of the order of 90° C. by means of a circulating or evaporating coolant fed to the reactor through a line 26 and recovered through a line 27.

In the reactor 11 the ammonia and the ethylene oxide are reacted to form ethanolamines until not less than 50% and up to about 95% of the ethylene oxide has been converted; conversions of the order of 80% are preferred.

The reaction mixture is then fed to the reactor 12, of the adiabatic tubular type with a piston flow, where conversion of the ethylene oxide is completed, or practically completed, (greater than 99% conversion). The temperature in the reactor 12 rises to maximum values of the order of 180° C. and on average about 120° C.

The reaction products are then fed through a line 29 to the plate-type column 13, in which unreacted ammonia is removed together with part of the water.

The column 13 is operated at a pressure of from 0.5 to 1.0 kg/cm$^2$, with a temperature at the foot typically of the order of 90° C., maintained by a reboiler 34, heated by vapours leaving the top of the evaporator 14 through a line 35.

The aqueous ammoniacal vapours leaving the top of the column 13 through a line 30 contain approximately 50% by volume of ammonia, the remaining part consisting of water vapour, non-condensable gases and negligible quantities of ethanolamine, especially monoethanolamine.

These vapours are recycled to the ammonia absorption column 10 via falling-film condenser-absorption apparatus 31 cooled by a coolant circulated through lines 24 and 25, in which part of the vapours are condensed. The condensate obtained comprises the recycled aqueous ammoniacal solution which is fed to the column 10 by means of the line 20 and a pump 32, while the non-condensed gases, consisting for the most part of ammonia but with small quantities of water vapour and non-condensable gases, are fed to the column 10 through the line 17 and a compressor 33.

Referring again to the column 13 an aqueous solution of the ethanolamines formed in the reactors 11 and 12 is drawn off at the foot through a line 36 and fed by means of a pump 37 to an intermediate plate of the evaporator 14 which also comprises a plate-type column.

The evaporator is operated at a pressure greater than atmospheric and up to 1.5 kg/cm$^2$ absolute with a temperature at the foot of from 110° C. to 140° C. maintained by means of steam fed to the reboiler 50 through a line 38 and discharged through a line 39.

The aqueous vapour recovered through the line 35 at the head of the evaporator 14 is first used to heat the column 13, as described above, and condenses in the heat exchanger 34. The condensate is then recycled by means of a pump 44 and line 49 to the falling-film absorption-condensation apparatus 31 where it flows in equal current with the water-ammonia mixture fed through the line 30.

The ethanolamines recovered from the column 14 are drawn off through a line 40 with a water content not greater than 30% by weight and generally of the order of 20% by weight. The ethanolamines are subjected to complete dehydration in the plate-type column 15 which is operated at a bottom pressure of from 150 to 300 mmHg with a temperature at the foot of from 140° to 160° C.

The water vapour which is given off through a line 41 is condensed in a heat exchanger 42. The resulting condensate is in part refluxed into the column 15 through a line 43 and in part recycled to the evaporator 14 (line 48), as washing water for the ethanolamine vapour (principly mono-ethanolamine) contained in the gaseous flow rising up through the evaporator 14, and the remaining part is discharged through a line 19. The vacuum line for the column 15 is indicated at 45.

The ethanolamines, free from water, or at least having a water content of less than 0.5% by weight, are recovered at the foot of the column 15 by means of line 46 and pump 47 and may be conveyed directly to stock, or alternatively to a rectifying treatment to separate the individual components from the mixture obtained.

Referring to FIGS. 2 to 5 of the drawings, the absorption column 10 used in the process according to the invention described above is shown in greater detail.

The column 10 has a cylindrical wall 70 mounted with its axis substantially vertical and contains a hollow, axial shaft bounded by a cylindrical wall 53 and a plurality of spaced-apart annular plates generally indicated 71, coaxially surrounding and welded to the said wall 53.

Alternate plates 71a have an upstanding, fixed, outer rim 61 spaced from the outer wall 70 and closely surrounded by a cylindrical wall 64 having a serrated upper edge 52. The lower edge of the wall 64 is spaced above the plate 71b immediately below the respective plate 71a such that the annular space 72 between the walls 53 and 64 forms a duct through which liquid can flow from the upper plate 71a to the lower plate 71b. Each wall 64 is movable vertically within the column 10 by means of pins 65 slidable in cooperating, vertical slits in the respective rim 61, such that the height of the edges 52, which acts as a weir for liquid flowing across the respective plate 71a, and hence the depth of liquid on the plate is variable.

The outer edge of the alternate plates 71b are sealed to the wall 70 of the column 10 by means of respective annular gaskets 56 but a weir 55, of variable height, having a serrated upper edge is provided above the inner edge of each plate 71b. Each weir 55 allows access through two diametrically opposed openings in the wall 53 of the inner shaft to respective part-annular-section, vertical ducts 73 within the shaft, bounded by respective portions of the wall 53 and part-cylindrical walls 54. The lower end of each duct 73 is closed by a portion of a plate 71a which extends into the shaft such that each duct 73 can conduct liquid from a respective plate 71b on to the plate 71a immediately beneath it.

Liquid introduced into the column 10 at or near the head is thus forced to flow downwardly through the outer, annular ducts 72, radially-inwardly across the alternate plates 71b, down through the inner ducts 73 and radially outwardly across the alternate plates 71a, as shown in FIG. 2.

In addition, each plate 71 has equispaced bell turrets 62 through which gas, in this process ammonia, introduced at or near the foot of the column 10, can bubble upwardly to be absorbed in liquid flowing across the respective plate. The direction of gas flow is also shown in FIG. 2.

Cooling of fluids flowing through the absorption column 10 is effected by means of passing a coolant liquid through an annular cavity 63 in each plate 71. The coolant liquid is fed into each cavity 63 from a feed manifold 58 within the hollow shaft through take-off ducts 59 and is collected from each cavity through further ducts which open into an outflow manifold 57, again housed within the hollow shaft.

Figure 5:
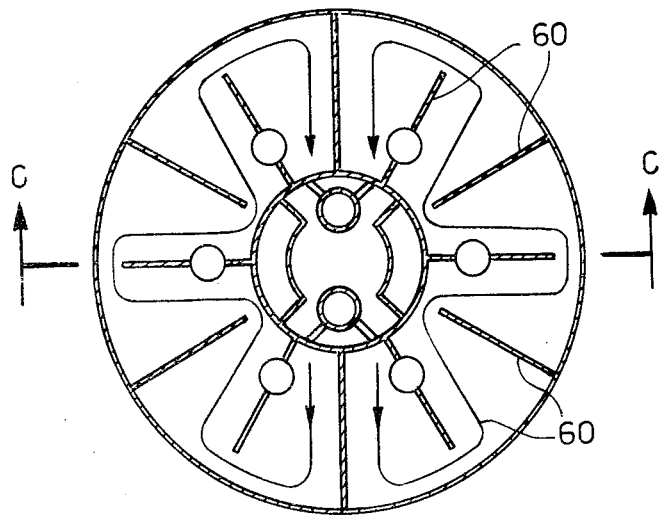
FIG. 5 is a horizontal sectional view taken on line B—B of FIG. 3.

The direction of flow of the coolant liquid within the cavities 63 is controlled by deflector plates 60 such as to ensure uniform cooling of the plates, as shown by the arrows in FIG. 5.

The column 10 described above has the particular advantage of being made in readily disengageable inner sections 66, shown in FIG. 1, which can simply be withdrawn from an outer shell of the column.

In use, with a suitable flow of the coolant, even the exothermal dissolution of ammonia in water required for the present invention can be ensured throughout the entire height of the column 10. Thus, the absorption of ammonia in water can be achieved in a plate column, even of small diameter such as is typical for absorption apparatus in average-sized ethanol-amine plants, the use of filled columns with their associated cooling problems being avoided.

A specific example of a process according to the invention will now be described, in which quantities are given as flow rates per hour.

EXAMPLE

Referring to FIG. 1 of the drawings ammonia is absorbed in water in the column 10 and a flow containing 30 Kmoles of ammonia and 52.5 Kmoles of water in pumped through the line 22 by the pump 39 to be mixed with 10 Kmoles of ethylene oxide fed through line 23. The mixture is thence conveyed to the isothermal reactor 11 with an input temperature of the mixture of 30° C.

The exothermic reaction of the ammonia with the ethylene oxide to form the required ethanolamines is carried out in the reactor 11 at a pressure of 15 kg/cm² abs., with a contact time of 25 minutes. The flow of coolant liquid through the lines 26, 27 is such as to ensure a temperature of the reaction mixture at the outlet from the reactor 11 of 90° C.

Under these conditions about 80% of the ethylene oxide is converted to ethanolamines.

The mixture leaving the reactor 11 is conveyed to the adiabatic reactor 12, consisting of an insulated coil, where the conversion of the ethylene oxide is practically completed over a period of 20 minutes. The temperature of the reaction mixture leaving the reactor 12 is about 120° C. and the mixture contains 3.21 Kmoles of mono-ethanolamine, 1.70 Kmoles of di-ethanolamine, 1.13 Kmoles of tri-ethanolamine as well as about 23.95 Kmoles of ammonia, 52.5 Kmoles of water and small quantities of higher-boiling substances.

The reaction mixture is conveyed through the line 29 to the head of the apparatus 13 for the desorption of the ammonia, comprising a column having 20 actual plates operating with a pressure at the head of 0.76 kg/cm² abs. A gaseous flow containing all the ammonia in the feed to the said column 13 together with 20 Kmoles of water and negligible quantities of ethanolamines is taken off from the head through the line 30. A liquid flow, practically devoid of ammonia, and consisting of the ethanolamines in the feed mixture and the remaining quantity of water (32.5 Kmoles), is extracted from the bottom of the column 13 through the line 36.

The heat necessary for the desorption of the ammonia and for the evaporation of the water is provided by means of the reboiler 34 and the temperature at the bottom of the column is about 97° C.

The liquid flow is conveyed through the line 36 by means of the pump 37 to the evaporator 14 which comprises a column having 10 actual plates and incorporating a reboiler 50, the liquid feed being introduced at the height of the sixth plate from the head.

The pressure at the head of the evaporator 14 is about 1.15 kg/cm² abs.

Water is evaporated in the evaporator 14, the vapour ascending to the head of the column where it is washed by a flow of washing water introduced through the line 48 to recover small percentage of ethanolamines contained therein. The molar ratio between the washing water and the ascending water vapour is about 4/30.

A flow of water vapour (about 30.5 Kmoles) which is practically pure leaves the head of the evaporator 14 through the line 35 and is condensed in the reboiler 34 of the desorption apparatus 13 to provide heat for the latter.

Saturated water vapour is fed to the reboiler 50 through the line 38 at a pressure of 5 kg/cm² abs. as the heating fluid.

The temperature at the bottom of the column 14 is about 125° C. and the effluent leaving the bottom through the line 40 contains practically the entire quantity of the ethanolamines produced in the reactors 11, 12 and about 17% by weight of water. This effluent is fed to the rectifying column 15 having 18 actual plates, at the height of the eighth plate from the head.

The column 15 is operated with a reflux ratio of about 0.6/1, a temperature at the bottom of about 160° C. and a pressure of about 300 mmHg, and the mixture of the ethanolamines is extracted from the bottom through the line 46 with the following molar composition: 53% mono-ethanolamine, 28.3% di-ethanolamine, 18.6% tri-ethanolamine, 0.1% water and high boiling products.

About ⅓ of the condensate discharged from condenser 42 through pipe 51 is drained off through the line 19 while the remaining part (about ⅔) is conveyed by gravity as the washing liquid for the evaporator 14.

Returning to the desorption apparatus 13, the gaseous flow of ammonia and water vapour issuing from the head is conveyed through line 30 to the falling film absorption-condensation apparatus 31 which is cooled by liquid flowing through the lines 24 and 25. In addition, the water condensed in the reboiler 34 for the column 13 is conveyed to the apparatus 31 through the line 49 by means of the pump 44 and is passed through said apparatus in equal flow with the flow of water vapour and ammonia.

The operating pressure of the apparatus 31 is about 0.75 Kg/cm² abs. and an ammoniacal solution is extracted from the bottom of the apparatus 31 through the line 21 with an ammonia content of about 25% molar.

A gaseous flow is also extracted consisting essentially of ammonia in quantities of about 7 Kmoles. This flow is compressed to about 2 kg/cm² abs. in the compressor 33.

Both the liquid flow and the gaseous flow from the apparatus 31 are conveyed to the absorption column 10 where they are used in the preparation of the ammoniacal solution used as a reactant in the present process.

In particular, this column 10 contains 40 plates spaced apart from each other by about 20 cm, the temperature of the liquid on the plates is about 30° C. and the operating pressure is 2 kg/cm² abs.

The non-condensable gases are exited from the top of the column 10 through the line 21, while make-up water is introduced at the head through the line 18 in quantities nearly equal to that drained through the line 19. The line 20 carrying the solution poor in ammonia opens into the column at the eighth plate from the head while the gaseous flow of ammonia compressed by means of the apparatus 33 is passed into the column at the twenty-fifth plate from the head. The fresh ammonia (about 6 Kmoles) is fed in at the height of the bottom plate and, lastly, the aqueous ammoniacal solution with a molar concentration of ammonia equal to about 36.3% is extracted at the bottom through the line 22.

Within the column 10 the descending liquid which is enriched gradually in ammonia, flows in counter-current with the flow of gaseous ammonia which becomes enriched in non-condensable gases. The optimal conditions for obtaining high concentrations of ammonia in the solution at the outlet are achieved.

What is claimed is:
1. A process for the preparation of ethanolamines by ammonolysis of ethylene oxide with aqueous ammonia and for the recovery of said ethanolamines, which comprises the steps of:
(a) preparing an aqueous ammoniacal solution containing from 20-50% by weight of ammonia by passing ammonia through an absorption column of the bubbling-tray type operating at a temperature of from 10° C. to 40° C. and at an absolute pressure of from 1.5 to 5 kg/cm², in counter-flow with water and a recycled aqueous ammoniacal solution, each of the bubbling-trays being individually cooled to maintain the absorption temperature within the range of from 10° to 40° C.;

(b) reacting said aqueous ammoniacal solution prepared in stage (a) with ethylene oxide in an isothermal reactor at a temperature of from 50° to 110° C., at an absolute pressure of from 10 to 30 kg/cm$^2$ and with an ammonia/ethylene oxide molar ratio of from 1/1 to 8/1, until at least 50% conversion of the ethylene oxide is achieved;

(c) feeding the reaction product of stage (b) into an adiabatic reactor and continuing the ammonolysis reaction until the conversion of said ethylene oxide to said ethanolamines is substantially complete, said ammonolysis reaction being carried out with a maximum temperature at the outlet from said adiabatic reactor of the order of 180° C.;

(d) removing the unreacted ammonia and a proportion of the water present in the reaction product of stage (c) by heating at an absolute pressure of from 0.5 to 1.0 kg/cm$^2$, condensing the aqueous ammoniacal vapors thus evolved, and recycling the aqueous ammoniacal solution thus obtained to stage (a);

(e) evaporating water from the residual aqueous solution of ethanolamines recovered in stage (d) in an evaporator at a pressure slightly greater than atmospheric and recycling the water vapour produced to provide heat for use in stage (d), and recovering a solution of ethanolamines having a water content not greater than 30% by weight; and (f) dehydrating said solution of ethanolamines recovered in stage (e) in a distillation column operated at a pressure lower than atmospheric, condensing the distillate from the head and using a part of the resulting condensate to wash the vapors at the head of said evaporator in stage (e) with consequent removal of the ethanolamine vapors contained therein, and recovering the dehydrated ethanolamines at the foot of said distillation column.

2. The process of claim 1, wherein stage (a) is carried out at a temperature of the order of 25° C. until said aqueous ammoniacal solution obtained contains approximately 35% by weight of ammonia.

3. The process of claim 1, wherein stage (b) is carried out at a temperature of the order of 90° C. with an ammonia/ethylene oxide molar ratio of approximately 3:1 until from 50% to 95% of said ethylene oxide is converted into said ethanolamines.

4. The process of claim 3, wherein stage (b) is continued until substantially 80% of said ethylene oxide is converted into said ethanolamines.

5. The process of claim 1, wherein stage (c) is carried out at a temperature of up to 120° C.

6. The process of claim 1, wherein stage (d) is carried out in a desorption column maintained at a bottom temperature of the order of 90° C.

7. The process of claim 1, wherein stage (e) is carried out at a pressure greater than atmospheric and up to 1.5 kg/cm$^2$ abs. with a temperature at the bottom of said evaporator of from 110° to 140° C. until the water content in said solution of ethanolamines is approximately 20% by weight.

8. The process of claim 1, wherein stage (f) is carried out at a pressure of from 150 to 300 mmHg, with a temperature at the bottom of the distillation column of from 140° to 160° C.

* * * * *